United States Patent [19]

Maurer et al.

[11] Patent Number: 4,619,918
[45] Date of Patent: Oct. 28, 1986

[54] TRIAZOLYL THIONOPHOSPHATES AND INSECTICIDAL AND NEMATICIDAL USE THEREOF

[75] Inventors: Fritz Maurer, Wuppertal; Bernhard Homeyer, Leverkusen, both of Fed. Rep. of Germany

[73] Assignee: Bayer Aktiengesellschaft, Leverkusen, Fed. Rep. of Germany

[21] Appl. No.: 794,815

[22] Filed: Nov. 4, 1985

[30] Foreign Application Priority Data

Nov. 9, 1984 [DE] Fed. Rep. of Germany ....... 3440913

[51] Int. Cl.[4] .......................... A01N 57/16; C07F 9/65
[52] U.S. Cl. ........................................ 514/93; 548/118
[58] Field of Search ........................... 548/118; 514/93

[56] References Cited

U.S. PATENT DOCUMENTS 3,867,396 2/1975 Dawes et al. ....................... 548/118
4,081,535 3/1978 Fuchs et al. ..................... 548/118 X
4,229,444 10/1980 Hoffmann et al. ............. 548/118 X
4,233,293 11/1980 Fuchs et al. .................... 548/118 X Primary Examiner—Richard L. Raymond
Attorney, Agent, or Firm—Sprung Horn Kramer & Woods

[57] ABSTRACT

Insecticidally and nematicidally active novel triazol-3-yl thionophosphates of the formula

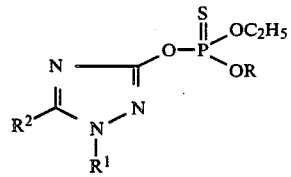

in which
  R represents i-propyl or sec.-butyl,
  $R^1$ represents alkyl or aryl and
  $R^2$ represents halogen.

8 Claims, No Drawings

TRIAZOLYL THIONOPHOSPHATES AND INSECTICIDAL AND NEMATICIDAL USE THEREOF

The invention relates to new triazol-3-yl-thionophosphates, a process for their preparation, and their use in pest-combating agents, in particular as insecticides and nematicides.

It is known that certain thionophosphates, such as, for example, O,O-diethyl O-(5-chloro-1-i-propyl-1,2,4-triazol-3-yl)thionophosphate, have an insecticidal activity (see DE-AS (German Published Specification) No. 2,260,015).

However, the duration of action of these compounds is not always completely satisfactory.

New triazol-3-yl-thionophosphates of the formula (I)

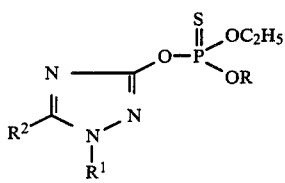

in which
R represents i-propyl or sec.-butyl,
$R^1$ represents alkyl or aryl and
$R^2$ represents halogen, have now been found.

Furthermore, it has been found that the new triazol-3-yl thionophosphates of the formula (I) are obtained when 3-hydroxytriazoles of the formula (II)

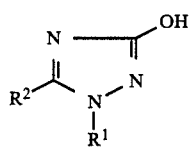

in which
$R^1$ and $R^2$ have the meanings given above, or the corresponding alkali metal, alkaline earth metal or ammonium salts, are reacted with halides of the formula (III)

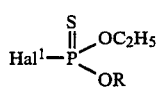

in which
R has the meaning given above, and
$Hal^1$ represents halogen, such as chlorine or bromine, if appropriate in the presence of an acid acceptor and, if appropriate, in the presence of a diluent.

The new triazol-3-yl-thionophosphates of the formula (I) are surprisingly distinguished by a particularly high and long-lasting activity as pest-combating agents, in particular as insecticides and nematicides.

The invention preferably relates to compounds of the formula (I) in which
R represents i-propyl or sec.-butyl,
$R^1$ represents alkyl having 1 to 6 atoms or aryl having 6 to 10 atoms and
$R^2$ represents halogen, preferably chlorine or bromine.

Particularly preferred compounds of the formula (I) are those in which
R represents i-propyl or sec.-butyl,
$R^1$ represents alkyl having 1 to 4 carbon atoms (such as, in particular, methyl, ethyl, n-propyl, i-propyl, n-butyl, i-butyl, sec.-butyl and tert.-butyl) or represents aryl having 6 carbon atoms, such as, in particular, phenyl, and
$R^2$ represents chlorine or bromine, preferably chlorine.

Very particularly preferred compounds of the formula (I) are those in which
R represents i-propyl or sec.-butyl, preferably i-propyl,
$R^1$ represents i-propyl, tert.-butyl or phenyl, preferably i-propyl, and
$R^2$ represents chlorine.

If, for example, O-ethyl-O-i-propyl-thionophosphoric acid diester chloride and 5-chloro-3-hydroxy-1-i-propyl-1,2,4-triazole are used as starting materials for the process according to the invention, the reaction can be represented by the following equation:

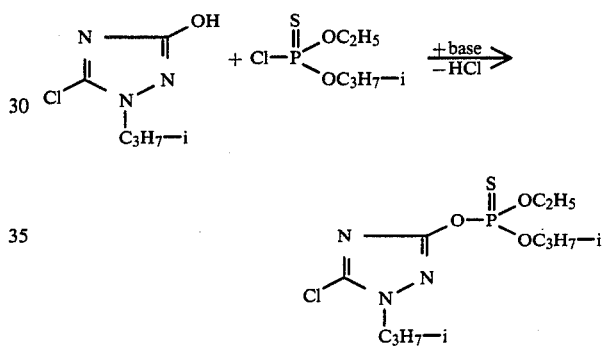

Formula (II) gives the definition of the 3-hydroxy-1,2,4-triazoles, or the corresponding alkali metal, alkaline earth metal or ammonium salts, to be employed in the process according to the invention, as starting materials for the preparation of the new compounds of the formula (I). In this formula, $R^1$ and $R^2$ represent those radicals which are specified above in formula (I) in the definition. Preferably used alkali metal or alkaline earth metal salts are the sodium, potassium or calcium salts, and preferably used ammonium salts are the ammonium or tri-(lower)-alkylammonium salts, such as trimethylammonium or triethylammonium salts.

The compounds of the formula (II) are known and/or can be prepared by generally known processes and methods (see, for example, DE-AS (German Published Specification No. 2,260,015)).

The following may be mentioned as examples of the compounds of the formula (II):

TABLE 1

| | | | (II) |
|---|---|---|---|

| $R^1$ | $R^2$ | $R^1$ | $R^2$ |
|---|---|---|---|
| $CH_3$ | Cl | $CH_3$ | Br |

TABLE 1-continued $$\underset{R^1}{\overset{\underset{R^2}{\overset{N}{\|}}}{N}}\underset{\underset{R^1}{|}}{\overset{OH}{\underset{N}{\|}}}\overset{\|}{N} \quad (II)$$

| R¹ | R² | R¹ | R² |
|---|---|---|---|
| C₂H₅ | Cl | C₂H₅ | Br |
| n-C₃H₇ | Cl | n-C₃H₇ | Br |
| i-C₃H₇ | Cl | i-C₃H₇ | Br |
| n-C₄H₉ | Cl | n-C₄H₉ | Br |
| i-C₄H₉ | Cl | i-C₄H₉ | Br |
| sec.-C₄H₉ | Cl | sec.-C₄H₉ | Br |
| tert.-C₄H₉ | Cl | tert.-C₄H₉ | Br |
| 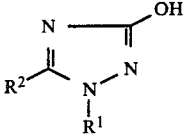 | Cl |  | Br |

Formula (III) gives a definition of the halides furthermore to be employed as starting materials. In this formula, R represents those radicals which are specified in formula (I) in the definition. In this formula Hal¹ represents halogen, such as, in particular, chlorine or bromine.

The compounds of the formular (III) are known.

The following may be mentioned as examples of the halides of the formula (III):
O-ethyl-O-i-propyl- and O-ethyl-O-sec.-butyl-thionophosphoric acid ester chloride and bromide.

The process, according to the invention, for the preparation of the new triazol-3-yl-thionophosphates of the formula (I) is preferably carried out using diluents. Suitable diluents are virtually all inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene or o-dichlorobenzene, ethers, such as diethyl ether and dibutyl ether, glycol dimethyl ether and diglycol dimethyl ether, tetrahydrofuran and dioxane, ketones, such as acetone, methyl ethyl, methyl isopropyl ketone and methyl isobutyl ketone, esters, such as methyl acetate and ethyl acetate, nitriles, such as, for example, acetonitrile and propionitrile, amides, such as, for example, dimethyl formamide, dimethyl acetamide and N-methyl pyrrolidone, and dimethyl sulfoxide, tetramethylene sulfone and hexamethyl phosphoric acid triamide.

The process can, if appropriate, be carried out in the presence of acid acceptors. All customary acid-binding agents can be used as acid acceptors. Alkali metal carbonates, such as sodium carbonate and potassium carbonate, alkali metal hydrides, such as sodium hydride, and aliphatic, aromatic or heterocylic amines, for example triethylamine, trimethylamine, dimethylaniline, dimethylbenzylamine and pyridine, have proved particularly useful.

The process according to the invention is carried out in general at temperatures between 0° C. and 100° C. The range between 20° C. and 80° C. is preferred. The reactions are carried out in general under atmospheric pressure.

To carry out the process according to the invention, the starting materials are usually employed in approximately equimolar amounts. An excess of either reactant does not have any substantial advantages. The reaction is carried out in general in a suitable diluent in the presence of an acid acceptor, and the reaction mixture is stirred for several hours at the required temperature. Thereafter, an organic solvent, for example toluene, is added, and the organic phase is worked up in a customary manner by washing, drying, and distilling off the solvent.

The new compounds are obtained in the form of oils, some of which cannot be distilled without decomposition, but can be freed from the last volatile constituents by so-called "incipient distillation", that is to say by prolonged heating to moderately elevated temperatures under reduced pressure, and can be purified in this manner. They are characterised by their refractive index.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Recticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,*

Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp, Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argar spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., and Tetranychus spp.

The *phytoparasitic nematodes* include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active components according to the invention, of the formula (I), are distinguished by an outstanding insecticidal and nematicidal activity. They are particularly suitable for use for the long-term combating of soil insects, such as, for example, *Diabrotica balteata* and *Phorbia antiqua,* aphids, such as, for example, *Myzus persicae,* and Nematodes, such as, for example, *Meloidogyne incognita.* A long duration of action is of very great practical importance for combating soil pests.

For this purpose, the active compounds can be applied directly into or on top of the soil. Parts of plants which are present in the soil or are introduced into the soil can also be treated with the active compounds or the pest-combating agents which contain the active compounds. Thus, for example, seed can be very advantageously protected, for example by dressing or incrustation.

The compounds according to the invention can furthermore be employed in combating hygiene pests or pests of stored materials.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is liquid solvents, liquefied gases under pressure, and/or solid carriers, optionally with the use of surface-active agents, that is, emulsifying agents and/or dispersing agents, and/or foam forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzene, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquified gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulation. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

EXAMPLE A

Long-term action test/soil insects

Test insect: *Phorbia antiqua* maggots
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (mg/liter), being decisive. The soil is filled into 5 liter pots and these are left to stand at 20° C.

After an interval of 2 weeks, and after prior renewed thorough mixing, soil samples of 250 cc are taken and the corresponding test insects are placed in the treated soil. After a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

The comparative test, for example at an active compound concentration of 2.5 ppm, gave the following result:

TABLE A

Long-term action/soil insects
*Phorbia antiqua* maggots in the soil

| Active compound | Degree of destruction in % at active compound concentration ppm after weeks/2.5 ppm Weeks | | | | |
|---|---|---|---|---|---|
| | 2 | 4 | 6 | 8 | 10 |
| 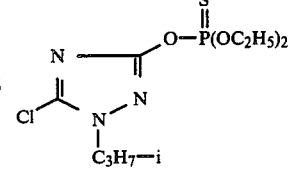 (A) (Known; see DE-A 2 260 015) | 100 | 100 | 100 | 50 | 0 |
| 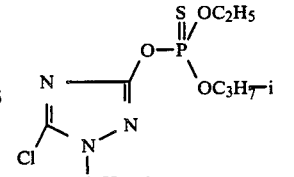 (1) | 100 | 100 | 100 | 100 | 100 |

EXAMPLE B

Long-term action test/soil insects

Test insect: *Diabrotica balteata* larvae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (mg/liter), being decisive. The soil is filled into 5 liter pots and these are left to stand at 20° C.

After an interval of 2 weeks, and after prior renewed thorough mixing, soil samples of 250 cc are taken and the corresponding test animals are placed in the treated soil. After a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

The comparative test, for example at an active compound concentration of 2.5 ppm, gave the following result:

TABLE B

Long-term action/soil insects
*Diabrotica balteata* larvae in the soil

| Active compound | Degree of destruction in % at active compound concentration ppm after weeks/2.5 ppm Weeks | | | | |
|---|---|---|---|---|---|
| | 2 | 4 | 6 | 8 | 10 |
| (A) (Known; see DE-A 2 260 015) — structure with S=P(OC₂H₅)₂, N, Cl, N-N, C₃H₇—i | 100 | 100 | 100 | 0 | 0 |
| (1) — structure with S, OC₂H₅, O—P, OC₃H₇—i, N, Cl, N-N, C₃H₇—i | 100 | 100 | 100 | 100 | 100 |

TABLE C

Long-term action/aphids
*Myzus persicae*

| Active compound | Degree of destruction in % at active compound concentration ppm after weeks/10 ppm Weeks | | | | |
|---|---|---|---|---|---|
| | 2 | 4 | 6 | 8 | 10 |
| (A) (Known; see DE-A 2 260 015) | 100 | 100 | 95 | 80 | 50 |
| (1) | 100 | 100 | 100 | 100 | 100 |

EXAMPLE C

Long-term action test/root-systemic action

Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into 3 liter pots and these are planted with cabbage (*Brassica oleracea*). The active compound can in this way be taken up from the soil by the roots of the plants and be transported into the leaves.

To demonstrate the root-systemic effect, the leaves are infested with the abovementioned test insects after 7 days. After a further 2 days, the evaluation is made by counting or estimating the dead insects. The root-systemic action of the active compound is deduced from the mortality figures. It is 100% if all the test insects have been killed and 0% if just as many test insects are still alive as in the case of the untreated control.

The comparative test, for example at an active compound concentration of 10 ppm, gave the following result:

EXAMPLE D

Long-term action test/nematodes

Test nematodes: *Meloidogyne incognita*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with the soil. The concentration of the active compound in the preparation is of practically no importance, only the weight of active compound per unit volume of soil, which is given in ppm (mg/l), being decisive. The soil is filled into 5 liter pots, which are left to stand at 20° C.

After 2 weeks, and after prior renewed thorough mixing, soil samples of 375 cc are taken, 125 cc of earth heavily infested with nematodes (Meloidogyne) are mixed with the treated soil, and these pots are cultivated at a greenhouse temperature of 25/18° C. with lettuce.

After three weeks the roots are examined for infestation by nematodes (root galls), and the degree of effectiveness of the active compound is determined as a %. The degree of effectiveness is 100% when infestation is completely avoided; it is 0% when the infestation is exactly the same as in the case of the control plants in untreated soil which has been infested in the same manner.

The comparative test, for example at an active compound concentration of 2.5 ppm gave the following result:

TABLE D

Long-term action/nematodes
*Meloidogyne incognita*

| Active compound | Degrees of destruction in % at active compound concentration in ppm after weeks 2.5 ppm Weeks | | | |
|---|---|---|---|---|
| | 2 | 4 | 6 | 8 |
| (A) (Known; see DE-A 2 260 015) | 100 | 75 | 0 | 0 |
| (1) | 100 | 100 | 100 | 75 |

(A) structure:
N—C(Cl)=... triazole with C₃H₇—i, bearing —O—P(=S)(OC₂H₅)₂

(1) structure:
N—C(Cl)=... triazole with C₃H₇—i, bearing —O—P(=S)(OC₂H₅)(OC₃H₇-i)

PREPARATION EXAMPLES

Example 1

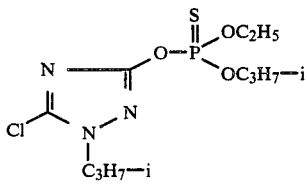

A mixture of 4.9 g (0.3 mol) of 5-chloro-3-hydroxy-1-i-propyl-1,2,4-triazole, 6.2 g (0.045 mol) of potassium carbonate, 6.1 g (0.03 mol) of O-ethyl-O-i-propyl-thionophosphoric acid diester chloride and 50 ml of acetonitrile is stirred for 18 hours at 20° C. to 25° C. After the addition of 300 ml of toluene the mixture is washed twice with 100 ml of water, the organic phase is dried over sodium sulphate, and the solvent is distilled off in vacuo. The residue is subjected to incipient distillation at 70° C. in a high vacuum.

7.2 g of (74% of theory) of O-ethyl O-i-propyl O-(5-chloro-1-i-propyl-1,2,4-triazol-3-yl)thionophosphate are obtained in the form of a colorless oil having a refractive index $n_D^{21}$ of 1.4829.

For example, the following compounds of the formula (I)

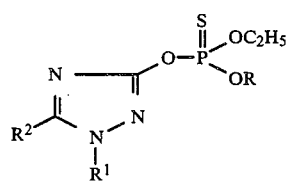

can be prepared analogously to Example 1:

| Example No. | R | R¹ | R² | Refractive Index |
|---|---|---|---|---|
| 2 | sec.-C₄H₉ | i-C₃H₇ | Cl | $n_D^{23}$: 1.4833 |
| 3 | i-C₃H₇ | tert.-C₄H₉ | Cl | |
| 4 | i-C₃H₇ | phenyl | Cl | |

It will be understood that the specification and examples are illustrative but not limitative of the present invention and that other embodiments within the spirit and scope of the invention will suggeest themselves to those skilled in the art.

We claim:

1. A triazol-3-yl thionophosphate of the formula

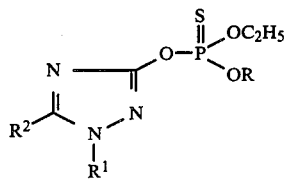

in which
R represents i-propyl or sec.-butyl,
R¹ represents alkyl or aryl and
R² represents halogen.

2. A compound according to claim 1, in which
R represents i-propyl or sec.-butyl,
R¹ represents alkyl having 1 to 6 atoms or aryl having 6 to 10 atoms and
R² represents halogen.

3. A compound according to claim 1, in which
R represents i-propyl or sec.-butyl,
R¹ represents alkyl having 1 to 4 carbon atoms or phenyl and
R² represents chlorine or bromine.

4. A compound according to claim 1, wherein such compound is O-ethyl O-i-propyl O-(5-chloro-1-i-propyl-1,2,4-triazol-3-yl)thionophosphate of the formula

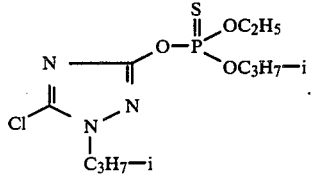

5. A compound according to claim 1, wherein such compound is O-ethyl O-sec.-butyl O-(5-chloro-1-i-propyl-1,2,4-triazol-3-yl)thionophosphate of the formula

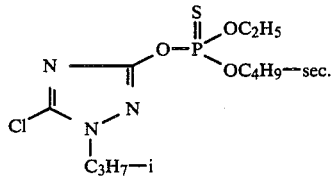

6. An insecticidal or nematicidal composition comprising an insecticidally or nematicidally effective amount of a compound according to claim 1 in admixture with a diluent.

7. A method of combating insects or nematodes which comprises applying to such insects or nematodes or to a habitat thereof an insecticidally or nematicidally effective amount of a compound according to claim 1.

8. The method according to claim 7, wherein such compound is
- O-ethyl O-i-propyl O-(5-chloro-1-i-propyl-1,2,4-triazol-3-yl)thionophosphate or
- O-ethyl O-sec.-butyl O-(5-chloro-1-i-propyl-1,2,4-triazol-3-yl)thionophosphate.

* * * * *